United States Patent [19]

Matthews

[11] 4,335,721

[45] Jun. 22, 1982

[54] TAMPON CONTAINING FUSIBLE PORTIONS

[75] Inventor: Billie J. Matthews, Menasha, Wis.

[73] Assignee: Kimberly-Clark Corporation, Neenah, Wis.

[21] Appl. No.: 234,674

[22] Filed: Feb. 17, 1981

[51] Int. Cl.³ .............................................. A61F 13/20
[52] U.S. Cl. .................................................. 128/285
[58] Field of Search .................... 128/285, 290 R, 296

[56] References Cited

U.S. PATENT DOCUMENTS 2,934,068  4/1960  Graham, Jr. et al. .............. 128/285
3,177,872  4/1965  Pearman .............................. 128/285
3,371,666  3/1968  Lewing ............................... 128/285

*Primary Examiner*—C. Fred Rosenbaum
*Attorney, Agent, or Firm*—Howard Olevsky; William D. Herrick

[57] ABSTRACT

A tampon having a series of parallelly aligned fibers is fused to a withdrawal string positioned transversely near one end of the fibers. The aligned fibers are then rolled in a jelly roll configuration in a manner which allows the free end of the withdrawal string to be centrally positioned at the bottom of the tampon at the inner end of the jelly roll.

8 Claims, 5 Drawing Figures

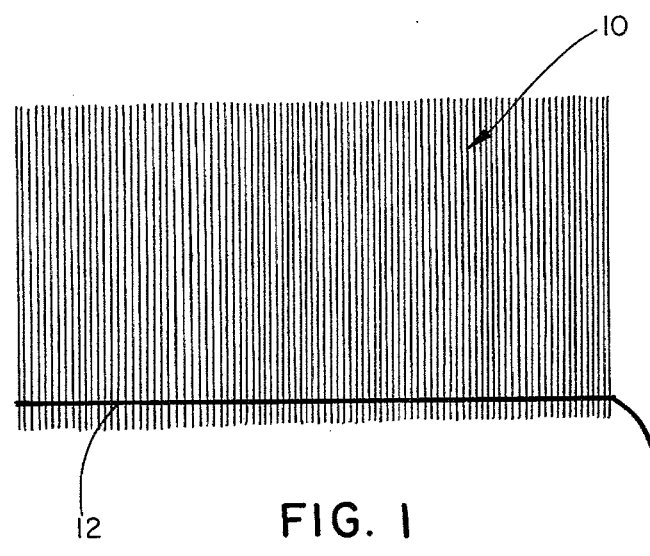
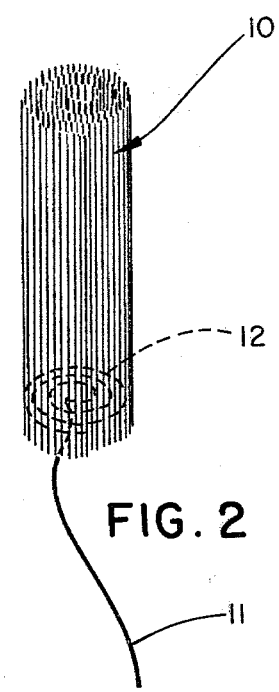
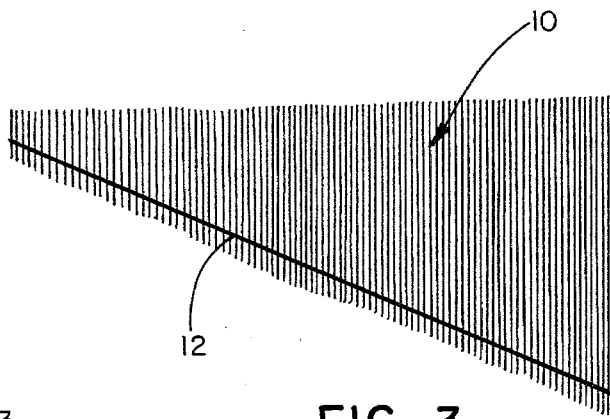
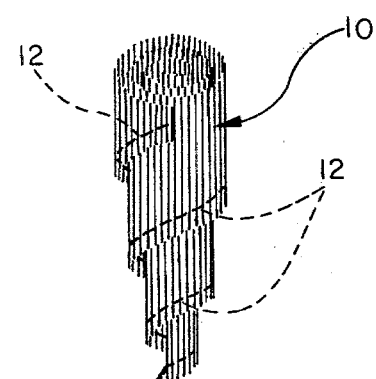
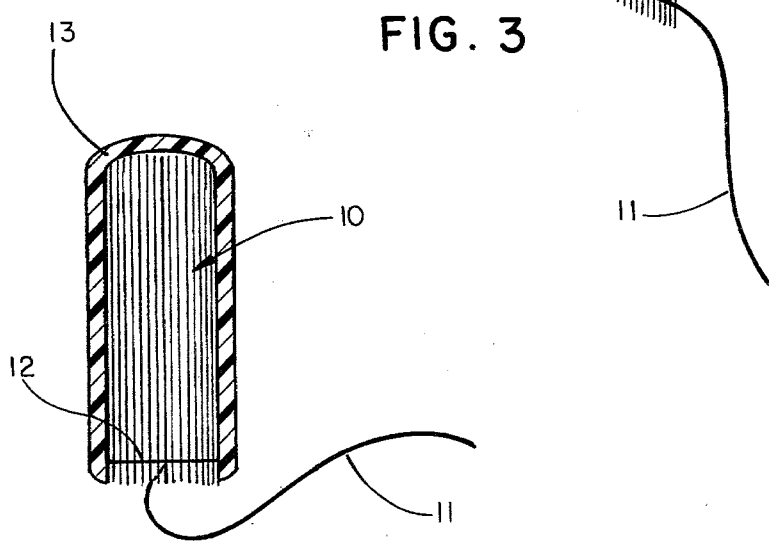

TAMPON CONTAINING FUSIBLE PORTIONS

BACKGROUND OF THE INVENTION

Conventional tampons are compressed cylindrical masses of absorbent fibers primarily cellulosic in nature. The tampons which are somewhat bullet-shaped are compressed to provide rigidity for ease of insertion and also to maximize the amount of absorbent material per cross sectional diameter available for absorbent purposes. When these conventional cellulosic materials are wetted by menses, the tampons swell and become more flexible however until this wetting occurs, leakage is possible between the inner walls of the vagina and the outer edges of the tampon.

Also the tampon manufacturing process is somewhat cumbersome in that it involves the steps of making a fibrous batt forming the batt into the appropriate shape compressing and heat setting to maintain the compressed configuration.

Attempts have been made in the past to produce a tampon which avoids the steps of compression and forming.

One of these approaches has been to utilize a porous foam-like material which while substantially more flexible and shape conforming does not absorb or maintain fluid as well as the conventional cellulosic materials.

Other attempts such as those disclosed in U.S. Pat. No. 2,934,068 and 3,320,956 teach the concept of producing a tampon solely with parallelly aligned fibers. In each of these instances, the fibers are folded and a withdrawal string is attached at the apex of the fold.

Another approach is that set forth in U.S. Pat. No. 3,986,511 which discloses in part a two component tampon system. The inner component is a rigid support body for an outer component which is one embodiment comprises a mixture of thermoplastic and nonthermoplastic fibers which are fused together in a fibrous mass which is supposedly soft and shape conforming. This patent involves several separate manufacturing steps in the production of the assembled composite product.

SUMMARY OF THE INVENTION

According to this invention a mass of parallelly aligned fibers are fused to a withdrawal string located transversely near one end of the fibers. The withdrawal string extends beyond the end of the fibers. The fibers are then rolled in a jelly roll configuration with the free unattached end of the withdrawal string located in the center of the roll. The ends of the fibers proximal to the withdrawal string are essentially equidistant from the withdrawal string and designed to be the end which forms the leading end on withdrawal of the tampon.

The subject invention can better be understood by reference to the drawings in which FIGS. 1 and 2 are representational examples of the product of this invention and its method of assembly; FIGS. 3 and 4 are representations of a second embodiment and FIG. 5 represents a particularly preferred feature of this invention.

As shown in FIG. 1 a series of fibers 10 are parallelly aligned and a withdrawal string 11 is placed transversely across the fibers at a position near one end. A segment of the withdrawal string is fused to the fibers by application of heat or ultrasonic means as desired to form a barrier seal 12. The tampon is rolled along a central axis defined by the direction of the fibers, the rolling occurring transversely to the longitudinal fiber orientation. As the mass of fibers is rotated about the axis the transverse rotation forms a jelly roll configuration having the seal line 12 located at the bottom of the rolled fibrous mass 10 with the free end of the withdrawal string 11 depending from the central rolled bottom portion of the fibrous mass. The seal line 12 forms a fluid barrier so that fluid entrapped in the interstices of the fibers or in a central area along the axis of the fiber mass will not flow beyond this seal.

Tampons made according to this invention can be designed for a variety of absorbencies depending upon the types and amount of fiber utilized and the density i.e. tightness of the fibrous cylinder.

Sealing on the bottom at the area of the withdrawal string can be accomplished by employing a fusible withdrawal string, a conventional withdrawal string coated with fusible thermoplastic powders and/or a fibrous mass containing fusible fibers.

It is desired that at least some of the fibers be fusible i.e. thermoplastic. Examples of suitable thermoplastic fibers include polyethylene, polypropylene, polyacrylonitrile, polyvinyl chloride, polyamide and polyester fibers. Polyolefin fibers are generally preferred from a cost standpoint, although certain polyester fibers have absorbent properties which are beneficial in tampons made according to this invention.

The same thermoplastics which are used as fibers can also be used as powder coatings or as single fiber for a withdrawal string.

Although thermoplastic fibers are generally considered nonabsorbent they can be rendered at least partially absorbent by the inclusion of surfactants. Surfactants which have proven to be particularly effective are Aerosol OT made by American Cyanamid Company, New York, New York, which is a dioctyl ester of sodium sulfosuccinic acid; TWEEN-20, a sorbitan mono laureate sold by ICI America, Wilmington, Delaware, and Igepal RC-520, a nonylphenoxypolyethyleneoxyethanol made by GAF Corporation of New York, New York.

While the amount of fusible fibers present may generally vary between 0 and 95%, it is currently preferred that the fusible fiber range between about 30 and 60% of the fibers present. The remaining fibers are preferably cellulosic in nature and especially preferred are rayon fibers. Any of the fibrous material conventionally used in tampons may be employed including superabsorbent fibers. Fiber length is a limiting feature, however. It is necessary for at least some fibers to be as long as conventional tampons, say 3-4 inches. Other fibers need only be long enough to provide for easy attachment to the withdrawal string. If fibers having variable lengths are utilized then location of the longer fibers on the interior of the jelly roll eases withdrawal of the tampon and is, therefore, preferred.

The alternative embodiment depicted in FIGS. 3 and 4 requires less long fibers i.e. about 10% of the fibrous mass than the embodiment depicted at FIGS. 1 and 2. According to FIG. 3 a fibrous tampon having a seal line 12 formed by fusing string 11 along fibers 10 is rolled in the same manner as illustrated in the preceding FIGS. A fibrous mass arranged so that the free end of the string 11 extends from an ordered arrangement of fibers positioned by fiber length as set forth. The fused seal is formed along a diagonal transverse line and rolled into the configuration shown at FIG. 4 producing a fibrous tampon with longer fibers in the center. While fusing occurs at the area of the withdrawal string, as stated previously, it is also preferred that some localized fusing occur throughout the fibrous mass to add some degree of rigidity and integrity to the mass itself. While fusing in the area of the string can be accomplished by ultrasonic means, selective fusing throughout the fibrous mass can best be accomplished by the localized low level application of microwave energy if rayon or cellulose fibers are present which absorb microwave energy and will heat the thermoplastic. Hot air blown through the fibers can also be utilized to provide local spots of selective fusing. An especially preferred alternative is to coat the fibrous mass with any of the conventional lubricants well known in the art. Solid water dispersible lubricants will provide structural integrity and lubrication; while not interfering with absorbency. When solid lubricants are employed, rolling may follow the application of the more flexible lubricants for ease of handling. Polyvinyl alcohol in sheet form is particularly adapted to this procedure and this approach to assembly is currently especially preferred. An example of a tampon having a solid lubricant is shown in FIG. 5 which is identical to FIG. 2 except for the presence of the lubricant cover 13.

While the fibers extend below the fusing lines to form a generally even end the precise planar configuration of the ends of the fibers it is not necessary nor is it necessary that all of the fibers be of equal length at the leading end of the tampon and it may be desirable to design fibers which are extended at the central portion after the tampon is rolled into its final configuration for ease of insertion.

It will be readily apparent by those with skill in the art that a tampon such as that described above can be altered to provide a variety of absorbencies and configurations and can be easily assembled and manufactured.

What is claimed is:

1. A tampon comprising in combination an absorbent matrix of parallelly aligned, closely packed fibers and a withdrawal string a portion of which is fusibly attached near one end of said fibers, said fibers having ends substantially equidistant from said withdrawal string near the points of attachment with said fibers also being transversely rolled to form a jelly roll configured cylindroidal fibrous mass.

2. A tampon according to claim 1 wherein the absorbent matrix contains fusible fibers.

3. A tampon according to claims 1 or 2 wherein the withdrawal string is fusible.

4. The tampon according to claim 1 wherein at least 10% of the fibers are between 3 and 4 inches long.

5. The tampon according to claim 1 wherein the pledget is a spiral of increasing length towards the center of the pledget after rolling.

6. The tampon according to claims 1, 2 or 4 wherein the fibers include superabsorbent.

7. The tampon according to claims 1, 2 or 4 wherein a solid, dispersible lubricant is coated over the outside of the pledget.

8. A process for making a tampon comprising:
   (a) positioning a plurality of fibers so that they are essentially aligned at one end and essentially parallel to each other;
   (b) positioning a withdrawal string transversely across a point essentially equidistant from the aligned end of the fibers;
   (c) fusing a portion of the withdrawal string to at least some of said fibers leaving an unattached portion of said string extending beyond an end of the aligned fibers; and
   (d) rolling said aligned fibers along their direction of alignment to form a jelly roll configuration thereby positioning the unattached end of the withdrawal string centrally in the fibrous cylindroidal mass.

* * * * *